US008865972B2

(12) United States Patent
Gabard et al.

(10) Patent No.: US 8,865,972 B2
(45) Date of Patent: *Oct. 21, 2014

(54) SULFONYLUREA-TOLERANT SUNFLOWER PLANTS

(75) Inventors: Jerome Gabard, Houssen (FR); Jean-Pierre Huby, Rixheim (FR)

(73) Assignee: E. I. du Pont de Nemours and Company, Wilmington, DE (US)

( * ) Notice: Subject to any disclaimer, the term of this patent is extended or adjusted under 35 U.S.C. 154(b) by 933 days.

This patent is subject to a terminal disclaimer.

(21) Appl. No.: 10/953,729

(22) Filed: Sep. 29, 2004

(65) Prior Publication Data

US 2005/0044587 A1  Feb. 24, 2005

Related U.S. Application Data

(62) Division of application No. 10/220,447, filed as application No. PCT/US01/05649 on Feb. 22, 2001, now Pat. No. 6,822,146.

(60) Provisional application No. 60/259,772, filed on Jan. 4, 2001, provisional application No. 60/237,597, filed on Oct. 3, 2000, provisional application No. 60/188,089, filed on Mar. 9, 2000.

(51) Int. Cl.
| | | |
|---|---|---|
| *A01H 1/00* | (2006.01) | |
| *A01H 5/00* | (2006.01) | |
| *A01H 5/10* | (2006.01) | |
| *C12N 9/88* | (2006.01) | |

(52) U.S. Cl.
CPC ... *C12N 9/88* (2013.01); *A01H 5/10* (2013.01)
USPC .......................... 800/300; 800/266; 800/322

(58) Field of Classification Search
None
See application file for complete search history.

(56) References Cited

U.S. PATENT DOCUMENTS

| | | | |
|---|---|---|---|
| 4,383,113 A | | 5/1983 | Levitt |
| 4,481,029 A | | 11/1984 | Levitt |
| 4,548,638 A | | 10/1985 | Hageman et al. |
| 4,673,648 A | * | 6/1987 | Wilcox et al. .................. 435/428 |
| 4,740,234 A | | 4/1988 | Lepone |
| 5,013,659 A | | 5/1991 | Bedbrook et al. |
| 5,084,082 A | | 1/1992 | Sebastian |
| 5,102,444 A | | 4/1992 | Liang |
| 5,476,524 A | | 12/1995 | Leon et al. |
| 5,605,011 A | * | 2/1997 | Bedbrook et al. ......... 47/58.1 R |
| 5,850,009 A | | 12/1998 | Kevern |
| 6,166,291 A | * | 12/2000 | Bidney et al. .................. 800/279 |
| 6,175,065 B1 | | 1/2001 | Schmidt et al. |
| 6,822,146 B2 | * | 11/2004 | Gabard et al. .................. 800/322 |

FOREIGN PATENT DOCUMENTS

| | | |
|---|---|---|
| WO | WO 03/012115 | 2/2003 |
| WO | WO 2008/024351 | 3/2006 |

OTHER PUBLICATIONS

White et al 1998 Proc. North Cent. Weed Sci. Soc. 53:96-97.*
Al-Khatib et al 1999, Proceedings of the 21st Sunflower Research Workshop, Jan. 14-15, 1999, National Sunflower Association, Bismark, N.D.*
Kolkman et al 2004, Theor. Appl. Genet. 109: 1147-1159.*
PI 633749 (*Helianthus annuus*, SURES-1, ARS-GRIN database, USDA, National Germplasm Resource Laboratory, Beltsville, Maryland), Jul. 20, 2007.*
W. Gottschalk & G. Wolff, *Induced Mutations in Plant Breeding*, Springer-Verlag, New York, 1983, particularly p. 12.
Al-Khatib Kassim et al., "Imazethapyr Resistance in common sunflower (*Helianthus annuus*)" Weed Science, vol. 46, No. 4, Jul. 1998, pp. 403-407, XP001024427.
Garcia-Torres L. et al., "Pre-emergence herbicides for the control of broomrape (*Orobanche cernua* Loefl.) in sunflower (*Helianthus annus* L.)." Weed Research, vol. 34 No. 6, 1994. pp. 395-402, XP001024426.
Anderson M D et al., "Weed Control in Sunflowers (*Helianthusannuus*) with Desmedipham and Phenmedipham" Weed Science, vol. 32, No. 3, 1984, pp. 310-314, XP001024428.
D. M. Joel, "Control of Broomrape (*Orobanche aegyptiaca* Pers.) with Chlorosulfuron on a Transgenic . . . ", WSSA Abstracts: 1992 Meeting of Weed Science Society of America, 1992, 32(65), 65.
D. M. Joel et al., Use of Transgenic Plants for Control of *Orobanche*:, Phytoparasitica, 1992, 20(4), 346.
J. Hershenhorn et al, "Effect of Sulfonylurea Herbicides on Egyptian Broomrape (*Orobanche aegyptiaca*) in Tomato . . . ", Weed Technology, 1998, 12, 115-120.
J. R. Qasem, "Chemical control of branched Broomrape (*Orobanche ramosa*) in glasshouse grown tomato", Crop Protection, 1998, 17(8), 625-630.
J. Hershenhorn et al., "*Orobanche aegyptiaca* control in tomato fields with sulfonylurea herbicides", Weed Research, 1998, 343-349.
J. Hershenhorn et al., "Effect of Sulfonylurea Herbicides on Early Development of Egyptian Broomrape (*Orobanche aegyptiaca*) in Tomato . . . ", Weed Technology, 1998, 12(1), 108-114.
J. R. Baumgartner et al., "Cross-Resistance of Imazethapyr-Resistant Common Sunflower (*Helianthus annus*) to Selected . . . ", Weed Technology, 1999, 13, 489-493.
A. D. White et al., "Evaluation of common sunflower (*Helianthus annuus* L.) resistance to acetolactate synthase inhibiting herbicides", Abstract 11.20, Abstract Meet. Weed Science Society of America 1998, 54.
Anderson, M. D. and W. E. Arnold (1984). "Weed control in sunflowers (*Helianthus annuus*) with desmedipham and phenmedipham." Weed Science 32: 310-314.
Baumgartner, J. R., K. Al-Khatib, et al. (1999). "Cross-resistance of Imazethapyr-resistant common sunflower (*Helianthus annuus*) to selected imidazolinone, sutfonylurea, and triazolopyrimidine herbicides." Weed Technol 13: 489-493.

(Continued)

Primary Examiner — David H Kruse

(57) ABSTRACT

This invention relates to sunflower lines and hybrids bred to contain a highly heritable trait conferring tolerance to sulfonylurea herbicides wherein said trait is conferred by an ALS gene encoding a sulfonylurea herbicide tolerant ALS enzyme and wherein the said sulfonylurea tolerant ALS enzyme is the sulfonylurea tolerant ALS enzyme encoded within the genome of certain designated sunflower lines.

23 Claims, No Drawings

(56) References Cited

OTHER PUBLICATIONS

Baumgartner, J. R., K. Al-Khatib, et al. (1999). "Survey of common sunflower (*Helianthus annuus*) resistance to imazethapyr and chlorimuron in northeast Kansas." Weed Technol 13: 510-514.

Boutsalis, P. and S. B. Powles (1995). "Inheritance and mechanism of resistance to herbicides inhibiting acetolactate synthase in *Sonchus oleraceus* L." TAG Theoretical and Applied Genetics 91(2): 242-247.

Bruniard, J. M. and J. F. Miller (2001). "Inheritance of imidazolinone-herbicide resistance in sunflower: ." Helia 24: 11-16.

Fabie, A. C. and J. Miller (2002). "Cross-Resistance of Two Sulfonylurea-Resistant Sunflower Sources to Selected Als Herbicides." Proc 24th Sunflower Research Workshop: 117-122.

Garcia-Torres, L., F. Lopez-Granados, et al. (1994). "Pre-emergence herbicides for the control of broomrape(*Orobanche cemue* Loefl.) in sunflower(*Helianthus annus* L.)." Weed research(Print) 34(6): 395-402.

Grula, J. W., R. L. Hudspeth, et al. (1995). "Organization, inheritance and expression of acebohydroxyacid synthase genes in the cotton allotetraploid *Gossypium hirsutum*." Plant Molecular Biology 28(5): 837-846.

Hu, J., J. F. Miller, et al. (2006). "Registration of a Tricatyledon Sunflower Genetic Stock." Crop Science 46(6): 2734.

Keeler, S. J., P. Sanders, et al. (1993). "Regulation of Tobacco Acetolactate Synthase Gene Expression." Plant Physiol. 102(3): 1009-1018.

Kolkman, J. M., M. B. Slabaugh, et al. (2004). "Acetohydroxyacid synthase mutations conferring resistance to imidazolinone or sulfonylurea herbicides in sunflower." TAG Theoretical and Applied Genetics 109(6): 1147-1159.

Marshall, M. W., K. Al-Khatib, et al. (2001). "Gene flow, growth, and competitiveness of imazethapyr-resistant common sunflower." Weed Science 49(1): 14-21.

Miller, J. and G. Seiler (2005). "Tribenuron Resistance in Accessions of wild sunflower collected in Canada." Proc 27th Sunflower Research Workshop.

Miller, J. F. and K. Al-Khatib (2004). "Registration of Two Oilseed Sunflower Genetic Stocks, SURES-1 and SURES-2 Resistant to Tribenuron Herbicide." Crop Sci 44(3): 1037-1038.

Olson, B. L. S., K. Al-Khatib, et al. (2004). "Distribution of Resistance to imazamox and tribenuron-methyl in native sunflower." http://www.sunflowernsa.com/research/research-workshop/documents/158.pdf.

Ouellet, T., R. G. Rutledge, et al. (1992). "Members of acetohydroxyacid synthase multigene family of *Brassica napus* have divergent patterns of expression." The Plant Journal 2(3): 321-330.

Sukno, S., J. Ruso, et al. (1999). "Interspecific hybridization between sunflower and wild perennial *Helianthus* species via embryo rescue." Euphytica 106(1): 69-78.

Volenberg, D. S., D. E. Sloltenberg, et al. (2001). "Biochemical mechanism and inheritance of cross-resistance to acetolactate synthase inhibitors in giant foxtail." Weed Science 49(5): 635-641.

White, A. D., M. A. Graham, et al. (2003). "Isolation of acetolactate synthase homologs in common sunflower." Weed Science 51(6): 845-853.

White, A. D., M. D. K. Owen et al. (1997). "Evaluation of common sunflower (*Helianthus annuus*) resistance to acetolactate synthase inhibiting herbicides." Weed Sci. Soc. Am. Abstr 38(11.20).

White A. D., M. D. K. Owen, et al. (1997). "Common sunflower resistance to acetolactate synthase inhibiting herbicides." Weed Science 50(4): 432-437.

Zelaya, I. A. and M. D. K. Owen (2004). "Evolved resistance to acetolactate inhibiting herbicides in common sunflower (*Helianthus annuus*), giant ragweed (*Ambrosia trifida*), and shattercane (*Sorghum bicolor*) in Iowa." Weed Science 52(4): 538-548.

Williams, D., Miller J., Letter/Memo to Sunflower Researchers,(May 7, 2001) Sunflower Releases for Spring-2001, North Dakota State University, Dept. of Plant Sciences.

\* cited by examiner

SEQUENCE LISTING

```
<160> NUMBER OF SEQ ID NOS: 1

<210> SEQ ID NO 1
<211> LENGTH: 655
<212> TYPE: PRT
<213> ORGANISM: Helianthus annuus

<400> SEQUENCE: 1

Met Ala Ala Pro Pro Asn Pro Ser Ile Ser Phe Lys Pro Pro Ser Pro
1               5                   10                  15

Ala Ala Ala Leu Pro Pro Arg Ser Ala Phe Leu Pro Arg Phe Ala Leu
            20                  25                  30

Pro Ile Thr Ser Thr Thr Gln Lys Arg His Arg Leu His Ile Ser Asn
        35                  40                  45
```

-continued

```
Val Leu Ser Asp Ser Lys Ser Thr Thr Thr Thr Thr Thr Thr Gln
    50                  55                  60

Arg Pro Leu Pro Val Gln Pro Phe Val Ser Arg Tyr Ala Pro Asp Gln
65                  70                  75                  80

Pro Arg Lys Gly Ala Asp Val Leu Val Glu Ala Leu Glu Arg Glu Gly
                85                  90                  95

Val Thr Asp Val Phe Ala Tyr Pro Gly Gly Ala Ser Met Glu Ile His
            100                 105                 110

Gln Ala Leu Thr Arg Ser Ser Thr Ile Arg Asn Val Leu Pro Arg His
        115                 120                 125

Glu Gln Gly Gly Val Phe Ala Ala Glu Gly Tyr Ala Arg Ala Ser Gly
    130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
                165                 170                 175

Ile Thr Gly Gln Val Leu Arg Arg Met Ile Gly Thr Asp Ala Phe Gln
            180                 185                 190

Glu Thr Pro Ile Val Glu Val Thr Arg Ser Ile Thr Lys His Asn Tyr
        195                 200                 205

Leu Val Leu Asp Val Glu Asp Ile Pro Arg Ile Val Arg Glu Ala Phe
    210                 215                 220

Tyr Leu Ala Ser Ser Gly Arg Pro Gly Pro Val Leu Ile Asp Val Pro
225                 230                 235                 240

Lys Asp Ile Gln Gln Gln Leu Val Val Pro Lys Trp Asp Glu Pro Met
                245                 250                 255

Arg Leu Pro Gly Tyr Leu Ser Arg Met Pro Lys Pro Gln Tyr Asp Gly
            260                 265                 270

His Leu Glu Gln Ile Val Arg Leu Val Gly Glu Ala Lys Arg Pro Val
        275                 280                 285

Leu Tyr Val Gly Gly Gly Cys Leu Asn Ser Asp Asp Glu Leu Arg Arg
    290                 295                 300

Phe Val Glu Leu Thr Gly Ile Pro Val Ala Ser Thr Leu Met Gly Leu
305                 310                 315                 320

Gly Ala Tyr Pro Ala Ser Ser Asp Leu Ser Leu His Met Leu Gly Met
                325                 330                 335

His Gly Thr Val Tyr Ala Asn Tyr Ala Val Asp Lys Ser Asp Leu Leu
            340                 345                 350

Leu Ala Phe Gly Val Arg Phe Asp Asp Arg Val Thr Gly Lys Leu Glu
        355                 360                 365

Ala Phe Ala Ser Arg Ala Lys Ile Val His Ile Asp Ile Asp Pro Ala
    370                 375                 380

Glu Ile Gly Lys Asn Lys Gln Pro His Val Ser Ile Cys Gly Asp Ile
385                 390                 395                 400

Lys Val Ala Leu Gln Gly Leu Asn Lys Ile Leu Glu Glu Lys Asn Ser
                405                 410                 415

Val Thr Asn Leu Asp Phe Ser Thr Trp Arg Lys Glu Leu Asp Glu Gln
            420                 425                 430

Lys Met Lys Phe Pro Leu Ser Phe Lys Thr Phe Gly Glu Ala Ile Pro
        435                 440                 445

Pro Gln Tyr Ala Ile Gln Val Leu Asp Glu Leu Thr Gly Gly Asn Ala
    450                 455                 460

Ile Ile Ser Thr Gly Val Gly Gln His Gln Met Trp Ala Ala Gln Phe
```

-continued

```
        465                 470                 475                 480
Tyr Lys Tyr Asn Lys Pro Arg Gln Trp Leu Thr Ser Gly Gly Leu Gly
                485                 490                 495
Ala Met Gly Phe Gly Leu Pro Ala Ala Ile Gly Ala Ala Val Ala Arg
                500                 505                 510
Pro Asp Ala Val Val Asp Ile Asp Gly Asp Gly Ser Phe Met Met
            515                 520                 525
Asn Val Gln Glu Leu Ala Thr Ile Arg Val Glu Asn Leu Pro Val Lys
            530                 535                 540
Ile Leu Leu Leu Asn Asn Gln His Leu Gly Met Val Val Gln Trp Glu
545                 550                 555                 560
Asp Arg Phe Tyr Lys Ala Asn Arg Ala His Thr Tyr Leu Gly Asn Pro
                565                 570                 575
Ser Lys Glu Ser Glu Ile Phe Pro Asn Met Val Lys Phe Ala Glu Ala
                580                 585                 590
Cys Asp Ile Pro Ala Ala Arg Val Thr Gln Lys Ala Asp Leu Arg Ala
            595                 600                 605
Ala Ile Gln Lys Met Leu Asp Thr Pro Gly Pro Tyr Leu Leu Asp Val
        610                 615                 620
Ile Val Pro His Gln Glu His Val Leu Pro Met Ile Pro Ala Gly Gly
625                 630                 635                 640
Gly Phe Ser Asp Val Ile Thr Glu Gly Asp Gly Arg Thr Lys Tyr
                645                 650                 655
```

SULFONYLUREA-TOLERANT SUNFLOWER PLANTS

CROSS-REFERENCE TO RELATED APPLICATIONS

This application is a continuation of U.S. application Ser. No. 10/220,447 filed Aug. 28, 2002, now issued as U.S. Pat. No. 6,822,146, which was the National Stage of International Application No. PCT/US01/05649, filed 22 Feb. 2001, which claimed priority benefit from U.S. Provisional Application Nos. 60/188,089, filed 9 Mar. 2000; 60/237,597, filed 3 Oct. 2000; and 60/259,772, filed 4 Jan. 2001.

FIELD OF INVENTION

This invention concerns sunflower plants and more particularly, sunflower seeds that have developed resistance to sulfonylurea herbicides through mutagenesis.

BACKGROUND OF THE INVENTION

Cultivated sunflower (*Helianthus annuus* L.) is a diploid species (2n=34) grown in many temperate, semi-dry regions of the world as a source of oil and confectionery seeds. Oil types of sunflowers contain 40 to 48 percent oil in the seed. Sunflower oil is valued as an edible oil, because of its high unsaturated fat level and light color. Sunflower oil is used for salads, cooking oil or for margarine. The protein content of sunflower meal prepared from seeds after oil extraction is useful as livestock feed. The seeds from both oil and confectionery varieties of cultivated sunflower are useful as bird food.

Only a relatively few herbicides have been found and developed for selective weed control in cultivated sunflower. These herbicides include alachlor, S-ethyl dipropylcarbamothioate (EPTC), ethalfluralin, trifluralin, pendimethalin, chloramben, imazamethabenz-methyl, sethoxydim and sulfentrazone. Additional weed control treatments are needed to provide a better spectrum of weed control and to reduce the development of weed resistance to herbicides.

Among the weeds insufficiently controlled by herbicides presently used in cultivated sunflower are members of the Orobanchaceae family. These weeds are obligate root holoparasites of a number of broadleaf plants, including sunflower. Particular *Orobanche* species afflicting sunflower include *Orobanche aegyptiaca* Pers., *O. ramosa* L., *O. minor* Sm., *O. cumana* Wallr. and *O. cernua* Loefl. *O. cumana* Wallr. and *O. cernua* Loefl. (alternative names for the same species) is a severe pest in sunflower in eastern Europe and has been spreading through southern Europe. *Orobanche* presents. a worldwide risk, and some species such as *O. minor* have appeared as exotics in the United States. *Orobanche* species are very difficult to eliminate, because, except for their flower parts, they live in the soil, and their seeds are minute, prolifically produced, easily dispersed and very long-lived. Thus, herbicides presently used in sunflower generally provide inadequate control.

Since the discovery of sulfonylurea herbicides over twenty years ago, over two dozen sulfonylureas have been commercially developed for selective weed control in a wide variety of crops (*The Pesticide Manual, Eleventh Edition*, C. D. S. Tomlin, ed., British Crop Protection Council, Surrey, U.K., 1997). Sulfonylurea herbicides. have as an essential molecular structural feature a sulfonylurea moiety ($-S(O)_2NHC(O)NH(R)-$). The sulfonyl end of the moiety is connected either directly or by way of an oxygen atom or an optionally substituted amino or methylene group to a cyclic or acyclic group. At the opposite end of the sulfonylurea bridge, the amino group, which may have a substituent such as methyl (R being $CH_3$) instead of hydrogen, is connected to a heterocyclic group, typically a symmetric pyrimidine or triazine ring, having one or two substituents such as methyl, ethyl, methoxy, ethoxy, methylamino, dimethylamino, ethylamino and the halogens. As the mode of action of sulfonylurea herbicides is inhibition of the enzyme acetolactate synthase (ALS) found in plants but not animals, sulfonylurea herbicides provide a valued combination of excellent efficacy against weeds and very low toxicity to animals.

While sulfonylureas have been developed for selective weed control in a variety of crops, ordinary varieties of cultivated sunflower are generally insufficiently tolerant for sulfonylureas to be useful for selective weed control in sunflower crops. However, preemergence application of a low dose (2 to 6 g/ha) of chlorsulfuron has been reported to result in 75-85% control of *O. cernua* with sunflower tolerance (L. Garcia-Torres et al., *Weed Research* 1994, 34, 395-402). Although sulfonylurea herbicides have thus been shown to have effect on *Orobanche* species, the sensitivity of ordinary varieties of sunflowers to sulfonylureas prevents use of higher application rates to give better control of *Orobanche*.

Greater application rates of sulfonylurea herbicides could be used to control *Orobanche* as well as other weed species if varieties of sunflower more resistant to sulfonylureas could be developed. To be easily incorporated in breeding programs combining desirable traits, the trait for sulfonylurea tolerance should be highly heritable (i.e. dominant or semi-dominant). Induced mutagenesis has been used to produce sulfonylurea resistance in soybeans, as discussed in U.S. Pat. No. 5,084, 082, but this approach has not been reported for sunflower, which has dissimilar seed morphology compared to soybean. Furthermore because 99% of induced mutations are recessive (W. Gottschalk & G. Wolff *Induced Mutations in Plant Breeding*, Springer-Verlag, New York, 1983, particularly p. 12), dominant mutations are extremely rare. To find dominant herbicide resistance mutations typically requires screening many thousands of mutagenized seeds.

Accordingly there is a need to be able to selectively control *Orobanche* and other weeds using sulfonylurea herbicides. Applicants have conducted an extensive research program to find dominant or semi-dominant mutant traits providing sulfonylurea resistance in cultivated sunflower.

SUMMARY OF THE INVENTION

This invention relates to a method for producing a sunflower line containing a highly heritable trait conferring tolerance to sulfonylurea herbicides, wherein the method comprises: (a) treating sunflower seeds with a mutagenic agent; (b) growing the treated seeds into mature plants to produce second-generation seeds; (c) harvesting the second-generation seeds; (d) germinating the second-generation seeds in the presence of an selectably effective amount of a sulfonylurea herbicide to select for survival only germinated seeds containing a trait conferring tolerance to the sulfonylurea herbicide; and (e) growing a surviving germinated seed into a mature plant to produce through self-pollination seeds of the sunflower line containing the heritable trait.

This invention also relates to a sunflower seed containing a highly heritable trait conferring tolerance to sulfonylurea herbicides, wherein the trait is obtained through mutagenesis. Another embodiment of this invention is a sulfonylurea-tolerant sunflower plant, a part thereof such as pollen or an ovule, or a tissue culture of regenerable cells therefrom, grown from the aforementioned sulfonylurea-tolerant seed. The aforementioned seed and plants may additionally contain other desirable traits, such as resistance to *Orobanche* parasitism.

Another aspect of the invention is a method for producing inbred sunflower seed having tolerance to sulfonylurea herbicides comprising crossing a first parent sunflower with a second parent sunflower plant and harvesting the resultant inbred seed, wherein the first and second parent sunflower plants have a highly heritable trait conferring tolerance to sulfonylurea herbicides, wherein the trait is obtained through mutagenesis. Related embodiments include an inbred sunflower seed produced by this method and an inbred sunflower plant, or a part thereof such as a seed, produced by growing the inbred seed. Still another aspect of the invention is a method for producing hybrid sunflower seed having tolerance to sulfonylurea herbicides comprising crossing a first parent sunflower with a second parent sunflower plant and harvesting the resultant hybrid sunflower seed, wherein the first or second parent sunflower plant has a highly heritable trait conferring tolerance to sulfonylurea herbicides, wherein the trait is obtained through mutagenesis. Related embodiments include a hybrid sunflower seed produced by this method and a hybrid sunflower plant, or a part thereof such as a seed, produced by growing the hybrid seed.

A further aspect of the invention pertains to a method for controlling undesired vegetation in a crop of the aforementioned sulfonylurea-tolerant sunflower plants, the method comprising applying to the locus of the vegetation an effective amount of a sulfonylurea herbicide. Embodiments of this aspect of the invention include a method for controlling *Orobanche* species parasitic to sunflower.

Additional aspects of the invention include methods for controlling volunteer sunflower plants. in a cereal crop by applying an effective amount of 2,4-dichlorophenoxyacetic acid (2,4-D) and in a sugar beet crop by applying an effective amount of a mixture of triflusulfuron-methyl and phenmedipham to the locus of the vegetation.

DETAILED DESCRIPTION OF THE INVENTION

In the description and examples that follow, a number of terms are used. To provide a clear and consistent understanding of the specification and claims, including the scope to be given such terms, the following definitions are provided:

"Plant": includes plant cells, plant protoplasts, plant cell tissue cultures from which sunflower plants can be regenerated, plant calli, plant clumps, and plant cells that are intact in plants or parts of plants, such as embryos, pollen, ovules, anthers, petals and other flower and seed parts, leaves, stems and roots including root tips, and the like.

"Variety or cultivar": refers to a group of plants within the species (e.g., *Helianthus annuus*) which share certain constant characteristics that separate them from the typical form and from other possible varieties within that species. While possessing at least one distinctive trait, a "variety" is also characterized by a substantial amount of overall variation between individuals within the variety, based primarily upon the Mendelian segregation of traits among the progeny of succeeding generations.

"Line": means a group of plants which display less variation between individuals, generally as a result of several generations of self-pollination. Also, a line can include a group of plants vegetatively propagated from a single parent plant, using tissue or cell culture techniques.

"Sunflower Seed": botanically referred to as an "achene"; means the combined components the pericarp and embryo.

"Maintainer Line": refers to an isogenic fertile male inbred line counterpart to the CMS line. A maintainer line has a normal cytoplasm, which allows breeding with the CMS line to obtain CMS progeny.

"Cytoplasmic male sterile (CMS) plant or inbred line": means a sunflower line that produces no viable pollen, i.e. a male sterile plant. Male sterility is inherited maternally, i.e. the male sterile plant is used as the female parent in a cross with pollen from another sunflower. CMS lines are produced by crossing a recurrent parent inbred line (as male) with a non-recurrent line having a cytoplasmic male sterility trait and then backcrossing to the recurrent line until a male sterile line that is homologous to the recurrent line in all other respects is developed. The recurrent line is then considered the maintainer. CMS lines are also referred to as female lines.

"Restorer Line": means a line possessing the gene or genes to restore male fertility or viable pollen to a sunflower hybrid or inbred line and progeny having a maternal cytoplasm that causes male sterility. This term along with a description of cytoplasmic male sterility is discussed by Fick, "Breeding and Genetics," in *Sunflower Science and Technology*, J. F. Carter ed., 1978, pp. 279-338.

The present invention pertains to sunflower lines having rare highly heritable sulfonylurea herbicide-tolerance traits obtained through chemically or physically induced mutagenesis and artificial selection. These lines are useful in developing commercial varieties of sunflower crops having resistance to sulfonylureas, and thus enable use of these effective and environmentally benign herbicides to selectively control undesired vegetation. Undesired vegetation that can be controlled by sulfonylurea herbicides in resistant sunflower varieties includes troublesome parasitic weeds such as *Orobanche* species.

Mutagenesis of sunflower can be induced by treatment with a variety of mutagenic agents known in the art, including physical mutagens such as X-rays, gamma rays, fast or thermal neutrons, protons, and chemical mutagens such as ethyl methanesulfonate (EMS), diethyl sulfate (DES), ethyleneimine (EI), propane sultone, N-methyl-N-nitrosourethane (MNU), N-nitroso-N-methylurea (NMU), N-ethyl-N-nitrosourea (ENU) and sodium azide.

Sunflower mutants resistant to sulfonylurea herbicides are then selected by treatment with a selectably effective amount one or more sulfonylurea herbicides. Many sulfonylurea herbicides can be used in selection treatments, including commercially used sulfonylurea herbicides such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron, metsulfuron-methyl, nicosulfuron, oxasulfuron, primisulfuron-methyl, prosulfuron, pyrazosulfuron-ethyl, rimsulfuron, sulfometuron-methyl, thifensulfuron-methyl, triasulfuron, tribenuron-methyl, trifloxysulfuron and triflusulfuron-methyl. A selectably effective amount is the amount of sulfonylurea herbicide that prevents growth of sunflower plants lacking a dominant or semi-dominant mutation conferring resistance to sulfonylurea herbicides. A selectably effective amount will depend upon the sulfonylurea herbicide used as selection agent and can be easily determined by testing using a gradation of sulfonylurea herbicide concentrations. The choice of selection herbicide will influence the spectrum of sulfonylurea herbicide resistance of the selected mutants, although cross-resistance is typical and some selected mutants may be more tolerant of other sulfonylurea herbicides than the sulfonylurea herbicide used as the selection agent. For efficient selection, sulfonylureas with strong activity against ordinary sunflower varieties are desirable. Thifensulfuron-methyl and metsulfuron-methyl work well for selecting sulfonylurea-resistant sunflower mutants.

Finding dominant herbicide resistance mutations typically requires screening many tens to hundreds of thousands of mutagenized seeds. Although such screening can be conducted using a variety of equipment and procedures known in the art, the "Large-Scale Hydroponic Screening System" described in U.S. Pat. No. 5,084,082 is particularly useful for recovering sunflower mutants resistant to sulfonylurea herbicides.

Many of the following Examples and Tests refer to sunflower inbred lines 'HA89A' and 'HA89B', collectively comprising 'HA89', alternatively identified as 'H89'. ('HA89A' is alternatively identified as 'H89A', and 'HA89B' is alternatively identified as 'H89B'.) 'HA89' was created at the U.S. Department of Agriculture's North Dakota Agricultural Experiment Station at Fargo, and was released to the public in October, 1971. 'HA89A' consists of the cytoplasmic male sterile inbred line of 'HA89'; 'HA89B' is the inbred line maintainer of 'HA89A'. 'HA89A' (also referred to as 'CMS H89A', 'CMS HA89A' and 'CMS HA89') is cytoplasmic male sterile based on material of P. Leclercq, "Une Stérilité Mâle Cytoplasmique Chez le Tournesol," *Ann. Amélior. Plantes* 1969, 19 (2), 99-106. To reproduce 'HA89A' requires the maintainer 'HA89B'.

The following Example 1 illustrates the formation of sunflower lines resistant to sulfonylureas through the process of induced mutagenesis and artificial selection. In this Example, the parent sunflower line used was 'HA89B'.

EXAMPLE 1

Preparation of Sunflower Lines Resistant to Sulfonylurea Herbicides

Part A—Determination of Optimum Mutagen Concentration

A small size experiment was set up to define the concentration of ethyl methanesulfonate (EMS) required to induce a significant number of mutations in sunflower plants, without significantly reducing plant fertility. Batches each consisting of 6000 seeds of 'HA89B' were incubated in 0.1 M potassium phosphate buffer (pH 5.6), supplemented with concentrations of EMS between 0 and 80 mM for 18 hours at room temperature, causing the seeds to swell. The seeds were rinsed in sodium thiosulfate for 1 minute to decompose the EMS, then in 5 consecutive water washes to eliminate EMS traces. The overall rinsing procedure lasted 5 hours. Seeds were dried for 2 hours at 25° C. using an airflow drier and then divided into sub-batches of 200 seeds each. To determine the effect of EMS on germination and plant branching, sub-batches were sown in flats right after drying and following 2, 4 and 6 days of storage at 4° C. after drying. Plant branching was used as a visual measure of mutation frequencies. Sub-batches from each EMS concentration were also sown in pots right after drying and grown to maturity to determine effect of EMS treatments on seed setting.

Based on these tests, concentrations of EMS ranging between 20 to 40 mM were found to provide optimal results with 'HA89B' seed. Germination efficiency of seeds treated with these EMS concentrations remained greater than 75% of that of untreated seeds. These concentrations appeared to give significant mutation frequencies, as more than half of the plants were branched, compared to about 12% of plants from untreated seeds. Also, more than half of the plants produced viable seed.

Part B—Large-scale Sunflower Mutagenesis and Selection

Batches containing 45,000 seeds each of 'HA89B' sunflower line were incubated in 0.1 M potassium phosphate buffer (pH 5.6) supplemented with 20, 25, 30 or 35 mM EMS for 18 hours at room temperature under continuous stirring, causing the seeds to swell. As referenced hereafter, the first generation of mutated seeds is identified as '$M_1$'. The seeds were rinsed in sodium thiosulfate for 1 minute to decompose the EMS, then in 5 consecutive water washes to eliminate EMS traces. The overall rinsing procedure lasted 5 hours. Seeds were dried for 2 hours at 25° C. using an airflow drier. Seeds, including seeds with a emerging root tip, were planted approximately 48 hours after the beginning of seed mutagenesis in four separate field plots using a pneumatic seed planter to avoid damaging swelled and germinated seeds. The field plots were located several kilometers from other sunflower fields to avoid cross-pollination with cultivated hybrids or inbred lines. Approximately 120,000 seedlings germinated from 180,000 sown seeds and about 100,000 plants grew to maturity. Sunflower heads from each individual plot were harvested at maturity, bulked and mixed thoroughly. The progeny seed are hereafter identified as '$M_2$' with the four batches specified as '$M_2$-1', '$M_2$-2', '$M_2$-3' and '$M_2$-4', corresponding to their '$M_1$' parents being treated with 35, 30, 25 and 20 mM EMS, respectively. The yield of $M_2$ seeds harvested from each $M_1$ field sub-plot is summarized in Table 1.

TABLE 1

Yields of $M_2$ Seeds

| $M_2$ batch | EMS Treatment Concentration | Yield (Number of Seeds) |
|---|---|---|
| $M_2$-1 | 35 mM | 182,600 |
| $M_2$-2 | 30 mM | 482,400 |
| $M_2$-3 | 25 mM | 184,000* |
| $M_2$-4 | 20 mM | 4,017,100 |

*Yield reduced because of heavy bird damage.

'$M_2$' seeds were seeded in individual hydroponic beds described as "Large-Scale Hydroponic Screening System" in U.S. Pat. No. 5,084,082 and treated with sulfonylurea herbicides. For each treatment, 10,000 seeds were added per bed. Triflusulfuron-methyl was found to be insufficiently active on sunflower to be an efficient selection agent. Most of the treatments used thifensulfuron-methyl at 20, 40 or 50 µg/L or rimsulfuron at 40 or 80 µg/L. Five plants showing resistance to sulfonylurea herbicides were found during various selection experiments; these are identified in Table 2.

TABLE 2

Name, origin, selection herbicide & frequency of confirmed sulfonylurea tolerant plants

| Name | From seed batch | Selected with | Selection frequency* |
|---|---|---|---|
| M7 | $M_2$-2 | thifensulfuron-methyl | $4.2 \times 10^{-6}$ |
| M11 | $M_2$-1 | thifensulfuron-methyl | $5.5 \times 10^{-6}$ |
| M12 | $M_2$-2 | thifensulfuron-methyl | $4.2 \times 10^{-6}$ |
| M14 | $M_2$-2 | thifensulfuron-methyl | $2.1$ to $4.2 \times 10^{-6}$ |
| E24 | $M_2$-1 | rimsulfuron | $5.5 \times 10^{-6}$ |

*Selection frequency is calculated as the ratio of surviving mutant plants compared to the total number of seeds sown and treated with the sulfonylurea selection agent.
M7 and M12 are presumed to have the same mutation origin.
M11 and E24 are believed to be different mutants.
The mutation relatedness of M14 is unknown, as it was not characterized further.

'M11' and 'E24' were selected from the same $M_1$ mutagenized seed batch, but with different sulfonylurea herbicides. As 'M11' was later found to be not tolerant to rimsulfuron, 'M11' and 'E24' were likely due to different mutagenesis events. 'E24' was sterile and not developed further. 'M14' was also sterile. Of the five rescued plants, only 'M7', 'M11' and 'M12' were fertile and could be developed through breeding. 'M7' and 'M12' may have come from the same mutation event.

Part C—Assay of Resistance of Acetolactate Synthase to Inhibition by Sulfonylurea Herbicides The resistance of acetolactate synthase (ALS) enzyme activity to inhibition by sulfonylurea herbicides was studied for both the mutant lines selected through artificial selection using sulfonylurea herbicides and their sulfonylurea-susceptible parent ('H89B'). Leaf tissue fragments were collected from the sunflower plants after growing them on horticultural soil without herbicide. The leaf tissues were then ground in liquid nitrogen and suspended in extraction buffer (100 mM potassium phosphate, 1 mM sodium pyruvate, 0.5 mM magnesium chloride, 0.5 mM EDTA, 10% (v/v) glycerol, 0.1 mM FAD, 10 mM cysteine, 1 mM leucine, 1 mM valine, pH 7.5). The supernatant was collected after centrifugation (15 min at 4° C.) of the tissue debris and then treated with an equal volume of saturated aqueous ammonium sulfate solution for 1 hour. The precipitated proteins were collected after centrifugation and re-suspended in buffer (50 mM potassium phosphate, 100 mM sodium pyruvate, 10 mM magnesium chloride, pH 7.25), and then desalted by elution with the resuspending buffer through a Sephadex® (Pharmacia) column. The desalted extracts were incubated for 1 hour at 37° C. with 100 or 1000 ppb of thifensulfuron-methyl or rimsulfuron. (These two herbicides were chosen because of their use as artificial selection agents in the hydroponic experiments.) The ALS activity remaining was then assayed.

Assays were initiated by adding enzyme solution (20 μL, included in final reaction mixture volume) and terminated by the addition of aqueous sulfuric acid (2.55% v/v; 50 μL). The acidified reaction mixtures were then heated for 15 minutes at 60° C. Creatine (1.445 % w/v; 30 μL) was added followed by α-naphthol (6.516% w/v, 90 μL), freshly prepared in aqueous sodium hydroxide (5 N) and kept in the dark. Solutions were again heated for 15 minutes at 60° C. Absorbances were measured at 540 nm wavelength at 30 minutes after the termination of the assay. Absorbances were adjusted by subtracting the average $A^{540}$ of zero-time controls (containing 25% aqueous acetonitrile in place of compound solution) to which acid had been added prior to enzyme. Enzyme activity was calculated relative to full-color controls containing 25% aqueous acetonitrile in place of test compound solution.

Each measurement of ALS activity was replicated six times, and the measured activities were averaged. Results listed in Table 3 are expressed as percent of ALS enzyme activity remaining compared to a control without herbicide.

TABLE 3

ALS Activity Remaining after Treatment with Sulfonylureas

| Herbicide used for ALS test | Plant source | ALS activity with 100 ppb herb. | ALS activity with 1000 ppb herb. |
|---|---|---|---|
| Thifensulfuron-methyl | H89B | 16% | 4% |
| | $M_2M7$ | 50% | 26% |
| | $M_2M11$ | 30% | 16% |
| | $M_2M12$ | 50% | 17% |
| | $M_2M14$ | 32% | 17% |
| Rimsulfuron | H89B | 8% | 4% |
| | $M_2E24$ | 35% | 25% |

The test results show the ALS enzymes of the mutant lines selected with thifensulfuron-methyl retained 2-6 times more activity than wild-type ALS from 'H89B' in the presence of thifensulfuron-methyl. The ALS enzyme of the mutant line selected with rimsulfuron retained 4-6 times more activity than wild-type ALS from 'H89B' in the presence of rimsulfuron. This test thus confirms that mutations rendering the ALS enzyme resistant to inhibition by sulfonylureas cause the mutant lines' resistance to sulfonylurea herbicides.

Utility

Sulfonylurea-resistant sunflower lines obtained through induced mutagenesis and artificial selection are useful as sources of herbicide resistance in sunflower breeding programs. Inbred lines are produced by selfing selected plants for several generations to produce inbred lines which breed true and are highly uniform. Sulfonylurea-tolerant lines such as 'M7', 'M11' and 'M12' derived from accepted maintainer lines such as 'H89B' are particularly useful, because they facilitate the transfer of monogenic dominant (highly heritable) resistance quickly and efficiently through conventional means without sacrificing agronomic traits and without need for extensive back-crossing.

For example, sulfonylurea-tolerant maintainer lines can be crossed with lines that are male-sterile, most commonly achieved in sunflower breeding through cytoplasmic male sterility, to produce male-sterile progeny having the sulfonylurea-tolerance trait. The cytoplasmic male sterility (CMS) trait is obtained by crossing domesticated *Helianthus annuus* L. (as male) with *H. petiolaris* Nutt. (P. Leclercq, "Une Stérilité Mâle Cytoplasmique Chez le Tournesol," *Ann. Amélior. Plantes* 1969, 19 (2), 99-106) or *H. maximiliani* Schrad. or *H. giganteus* L. (E. D. P. Whelan and W. Dedio, "Registration of Sunflower Germplasm Composite Crosses CMG-1, CMG-2, and CMG-3 ", *Crop Science* 1980, .20, 832) and then repeated backcrossing with the domesticated *H. annuus* (as male). CMS is the result of factors resulting from the cytoplasmic, as opposed to nuclear, genome. A variety of methods for conferring genetic male sterility are available in the art, see for example, U.S. Pat. Nos. 3,710,511, 3,861,709, 4,654,465, 4,727,219 and 5,432,068, and European Patent Publication 329,308-A and PCT publication WO 90/08828.

Highly heritable sulfonylurea herbicide tolerance can be used to produce experimental or commercial quantities of $F_1$ hybrid seeds. In such an application, a herbicide-resistant line (that is rendered male sterile through genetic, chemical or manual means) is planted (either interplanted or in separate rows) in the same field with a male restorer but herbicide-sensitive line. After pollination, the male parent is removed from the field with a sulfonylurea herbicide treatment that is selectively lethal to the restorer parent. The entire field (containing $F_1$ seeds born by the sulfonylurea-resistant female line) can then be bulk harvested without seed contamination from the restorer line.

Hybridization allows combining or "stacking" a highly heritable trait for sulfonylurea tolerance with other desirable traits, for example, faster maturity, drought tolerance, cold tolerance, increased seed yield, increased seed oil content, modification of composition of fatty acid constituents in oil, increased seed storage protein content, modification of amino acid content in seed storage proteins, dwarfism, resistance to lodging, resistance to insects and diseases caused by bacteria, fungi and viruses, and resistance to parasitic plants such as *Orobanche*. Desirable disease resistance traits which may be combined with a sulfonylurea-tolerance trait include resistance to rust (caused by *Puccinia helianthi*), downy mildew (caused by *Plasmopara halstedii*), charcoal rot (caused by *Macrophominia phasiolina*), phoma black stem (caused by *Phoma macdonaldii*), wilt/middle stock rot/head rot (caused by *Sclerotinia sclerotiorum*) and stem canker (caused by *Pho-*

*mopsis helianthi*). U.S. Pat. Nos. 5,276,264 and 5,461,171 describe sunflower plants having traits for lowered levels of saturated fatty acids in the seed oil. U.S. Pat. Nos. 4,627,192, 4,743,402, 5,866,765 and 5,866,766 describe sunflower lines and hybrids having traits for high oleic acid content in the seed oil. U.S. Pat. No. 5,959,175 describes a method for modifying the oil composition of sunflower through genetic regulation. U.S. Pat. Nos. 4,378,655 and 4,527,352 describe semi-dwarf and full-dwarf sunflower hybrids. *Orobanche* resistance traits are known and the heredity of genes providing resistance to *Orobanche* has been studied (see, for example, J. F. Miller & G. N. Fick, "The Genetics of Sunflower" in *Sunflower Technology and Production*, A. A. Schneiter ed., No. 35 in Agronomy Series, American Society of Agronomy, Madison, Wis., USA, 1997, particularly pp. 476-477, and the references cited therein).

Sunflower breeding has become an established art (see, for example, *Sunflower Science and Technology*, J. F. Carter ed., No. 19 in Agronomy Series, American Society of Agronomy, Madison, Wis., USA, 1978, particularly Chapter 9 (pp. 279-338), G. N. Fick, "Breeding and Genetics", Chapter 10 (pp. 339-369), E. D. P. Whelan, "Cytology and Interspecific Hybridization", and Chapter 11 (pp. 371-386), D. L. Smith, "Planting Seed Production", and *Sunflower Technology and Production*, A. A. Schneiter ed., No. 35 in Agronomy Series, American Society of Agronomy, Madison, Wis., USA, 1997, particularly Chapter 8 (pp. 395-439), G. N. Fick & J. F. Miller, "Sunflower Breeding", Chapter 9 (pp. 441-495), J. F. Miller & G. N. Fick, "The Genetics of Sunflower", Chapter 10 (pp. 497-558), C. C. Jan, "Cytology and Interspecific Hybridization", and Chapter 11 (pp. 559-593), D. L. Bidney & C. J. Scelonge, "Sunflower Biotechnology"). Sunflower can be bred by both self-pollination and cross-pollination techniques. The development of a hybrid sunflower variety involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with unrelated inbred lines to produce the hybrid progeny ($F_1$). During the inbreeding process in sunflower, the vigor of the lines decreases. Vigor is restored when two different inbred lines are crossed to produce the hybrid progeny ($F_1$). An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid sunflower plants can then be generated from this hybrid seed supply. Large-scale commercial sunflower hybrid production, as it is practiced today, requires the use of some form of male sterility system as described above.

Besides sexual breeding, sunflower plants can be propagated through tissue and cell culture techniques, which inherently preserve the genetic makeup of the original plant. However, the genome can also be altered while in cell culture through use of mutagenesis or well-known gene transfer techniques (e.g., *Agrobacterium tumafaciens* infection, ballistic particle bombardment). Essentially any plant tissue with cells capable of cell division can be used for plant propagation through tissue and cell culture techniques. Cultures can be started from embryos, pollen, ovules, anthers, petals and other flower and seed parts, leaves, stems and roots including root tips. Tissues taken from the vascular area of stems and roots are particularly suitable. U.S. Pat. Nos. 4,670,391, 4,670,392, 4,673,648, 4,681,849, 4,687,743 and 5,030,572 describe methods for regenerating sunflower plants from cell cultures derived from sunflower tissues. Thus, it is clear from the literature that the state of the art is such that these methods of obtaining sunflower plants from cell cultures and tissue cultures are now well known. Thus another aspect of this invention is to provide cells which upon growth and differentiation produce sunflower plants having a sulfonylurea-tolerance trait.

Sulfonylurea-tolerant sunflower varieties extend the utility of sulfonylurea herbicides and provide the sunflower farmer with more options for weed control. With fewer crop safety constraints, greater emphasis can be given to obtaining good control of problem weeds. Such weeds include parasitic weeds such the broomrapes (*Orobanche* spp.) and dodder (*Cuscuta* spp.). Broomrapes afflicting sunflower include *Orobanche aegyptiaca* Pers., *O. ramosa* L., *O. minor* Sm., *O. cumana* Wallr. and *O. cernua* Loefl. Dodder afflicting sunflower include *Cuscuta glomerata* Choisy, *C. indecora* Choisy and *C. pentagona* Engelm. Control of *Orobanche* species by sulfonylureas in sulfonylurea-resistant sunflower varieties is particularly valuable, as *Orobanche* has been difficult to control using herbicides sufficiently safe to ordinary sunflower varieties. Also, sulfonylurea-resistant sunflower varieties provide opportunity to combine herbicides that have complementary weed control spectra and different modes of action. Such herbicide mixtures enable the farmer to control additional weed species while reducing the risk of fostering herbicide-resistant weed biotypes, which could become prevalent from repeated use of herbicides with the same mode-of-action.

A selectively lethal sulfonylurea treatment can also be used to remove herbicide-sensitive rogue plants from sulfonylurea-resistant populations that have been contaminated through careless seed handling operations. Large-scale seed production fields can be easily cleared of rogues by spraying the entire field with a herbicide treatment that is lethal to herbicide sensitive plants.

A wide variety of sulfonylurea herbicides can be advantageously used to control weeds in sulfonylurea-resistant sunflowers, including amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulftiron-methyl, mesosulfuron, metsulfuron-methyl, nicosulfuron, oxasulfuron, primisulfuron-methyl, prosulfuron, pyrazosulfuron-ethyl, rimsulfuron, sulfometuron-methyl, thifensulfuron-methyl, triasulfuron, tribenuron-methyl, trifloxysulfuron and triflusulfuron-methyl. Although a particular sulfonylurea-resistant sunflower line will typically demonstrate appreciable tolerance to a variety of sulfonylureas, high levels of tolerance are most assured to the particular sulfonylurea used as the selection agent during artificial selection following induced mutagenesis. However, induced mutagenesis and artificial selection can also give high levels of tolerance to sulfonylureas other than that used as the selection agent.

Generally sulfonylurea herbicides are applied to sulfonylurea-resistant sunflowers at similar rates as for other crops. Sulfonylurea herbicides can be applied to sunflower crops pre-emergence and post-emergence. For control of many weeds, including parasites such as *Orobanche*, post-emergence application generally provides the greatest efficacy for a particular application rate. However, pre-emergence and seed coating applications may be helpful in combination with post-emergence treatments for *Orobanche* control. Also, dividing the applications into more than one treatment (i.e. split applications) can improve *Orobanche* control while reducing risk of phytotoxicity to the sunflower. One skilled in the art can readily determine application rates as well as timing necessary for the desired level of weed control and crop safety.

With the specifically disclosed sulfonylurea-resistant sunflower lines 'M7', 'M 11' and 'M12' and their hybrids, tribenuron-methyl, metsulfuron-methyl and ethametsulfuron-methyl are particularly useful for selective control of weeds including *Orobanche*. For effective weed control with adequate crop tolerance, tribenuron-methyl is generally applied in the range of 5 to 50 g/ha, with 8 to 40 g/ha preferred and 15 to 30 g/ha more preferred for most uses. For effective weed control with adequate crop tolerance, metsulfuron-methyl is generally applied in the range of 1 to 12 g/ha, with 2 to 10 g/ha preferred and 4 to 8 g/ha more preferred for most uses. For effective weed control with adequate crop tolerance, ethametsulfuron-methyl is generally applied in the range of 5 to 50 g/ha, with 10 to 40 g/ha preferred and 15 to 30 g/ha more preferred for most uses.

The following tests demonstrate the herbicide tolerance of sunflower varieties obtained from conventional breeding of sulfonylurea-resistant lines 'M7', 'M11' and 'M12' and weed control in these varieties using sulfonylurea herbicides.

Test A—Demonstration of Sulfonylurea Herbicide Resistance

In a small field trial, the sunflower varieties described in Table 4 were sprayed post-emergence with a variety of sulfonylurea herbicide treatments.

to sterilize the pollen according to the general method described in *Sunflower Science Technology*, J. F. Carter ed. (Number 19 in the series "Agronomy") pp. 339-386. This treatment enables maintainer plants to behave as CMS inbred lines and allows the production of heterozygous resistant hybrids, with the herbicide resistant source coming from the female side. Such crosses allowed evaluating the sexual effect of the mutation source when introduced on the female side of a cross as described in crosses C, D and E versus the male side of a cross as described in crosses F, G and H. Labels I, J and K identify third generation CMS mutant lines crossed with fourth generation maintainer lines to maintain the highly heritable mutant trait in a male sterile homozygous resistant environment. One skilled in sunflower breeding art understands the meaning of such crosses.

Broadcast post-emergence applications of formulated sulfonylurea herbicides were performed at the 6-leaf development stage using four randomly distributed replications. Application rates were chosen to match the usual use rates of these herbicides in the crops they are registered in Europe. All herbicides except for metsulfuron-methyl were sprayed in combination with Citowet® non-ionic ethoxylated alcohol at 0.25% volume of formulated product per volume of water applied per hectare.

The evaluation of the maximum (i.e. peak) injury to sunflower varieties by sulfonylurea herbicides was measured by visual ratings, which are listed in Table 5. A rating of 0% phytotoxicity means no crop injury. A rating of 15 to 20%

TABLE 4

Description of Sunflower Varieties, Including Mutant Inbred Lines and Hybrids

| # | NAME | DESCRIPTION |
|---|------|-------------|
| A | Hybrid control: H89A × RHA274 | USDA CMS H89A ("USDA" means United States Department of Agriculture; "CMS" means cytoplasm male sterile) crossed with restorer line USDA RHA274 |
| B | Inbred line control: H89A | USDA CMS H89A (cytoplasm male sterile inbred line) |
| C | GA-$M_4$M12 × RHA274 | Hybrid mutant with $M_4$ generation of mutant line M12 on female side |
| D | GA-$M_4$M11 × RHA274 | Hybrid mutant with $M_4$ generation of mutant line M11 on female side |
| E | GA-$M_4$M7 × RHA274 | Hybrid mutant with $M_4$ generation of mutant line M7 on female side |
| F | H89A × $M_4$M12 | USDA CMS H89A crossed with $M_4$ generation of mutant line M12 on male side |
| G | H89A × $M_4$M11 | USDA CMS H89A crossed with $M_4$ generation of mutant line M11 on male side |
| H | H89A × $M_4$M7 | USDA CMS H89A crossed with $M_4$ generation of mutant line M7 on male side |
| I | $BC_3$-$M_4$M12 | Third generation back-cross of inbred line mutant M12 |
| J | $BC_3$-$M_4$M11 | Third generation back-cross of inbred line mutant M11 |
| K | $BC_3$-$M_4$M7 | Third generation back-cross of inbred line mutant M7 |

To generate the hybrids C, D and E, the fourth generation self-pollinated maintainer mutant lines $M_4$M12, $M_4$M11 and $M_4$M7 were chemically sterilized by applying at the bud "star" flower stage a small amount of gibberellic acid solution injury, indicating the plants were not significantly adversely affected and rapidly and completely recovered, is the limit of injury considered acceptable by farmers. A rating of 100% means the complete destruction of all plants.

TABLE 5

Maximum Phytotoxicity Following Sulfonylurea Treatments

| Active Ingredient | Rate (g a.i./ha)* | A | B | C | D | E | F | G | H | I | J | K |
|---|---|---|---|---|---|---|---|---|---|---|---|---|
| Primisulfuron-methyl | 30 | 100 | 100 | 71 | 75 | 74 | 66 | 73 | 69 | 35 | 55 | 51 |
| Nicosulfuron | 30 | 33 | 54 | 12 | 13 | 13 | 15 | 20 | 16 | 8 | 23 | 14 |
| Rimsulfuron | 15 | 100 | 100 | 99 | 99 | 98 | 98 | 98 | 96 | 90 | 95 | 95 |

TABLE 5-continued

Maximum Phytotoxicity Following Sulfonylurea Treatments

| Active Ingredient | Rate (g a.i./ha)* | Sunflower Varieties | | | | | | | | | | |
|---|---|---|---|---|---|---|---|---|---|---|---|---|
| | | A | B | C | D | E | F | G | H | I | J | K |
| Rimsulfuron | 30 | 100 | 100 | 100 | 100 | 100 | 100 | 100 | 100 | 97 | 98 | 97 |
| Triflusulfuron-methyl | 20 | 100 | 100 | 19 | 19 | 20 | 16 | 15 | 10 | 4 | 6 | 8 |
| Triflusulfuron-methyl | 40 | 100 | 100 | 38 | 40 | 38 | 33 | 36 | 33 | 13 | 14 | 10 |
| Thifensulfuron-methyl | 35 | 100 | 100 | 75 | 81 | 83 | 78 | 81 | 80 | 34 | 52 | 36 |
| Thifensulfuron-methyl | 70 | 99 | 100 | 88 | 92 | 93 | 89 | 90 | 90 | 53 | 79 | 79 |
| Metsulfuron-methyl | 6 | 100 | 100 | 8 | 7 | 0 | 4 | 6 | 4 | 7 | 11 | 8 |
| Tribenuron-methyl | 22.5 | 100 | 100 | 0 | 6 | 2 | 0 | 3 | 0 | 4 | 0 | 4 |
| Triasulfuron | 20 | 100 | 100 | 94 | 99 | 97 | 98 | 98 | 98 | 93 | 95 | 95 |

*Application rates in treatments refer to amount of active ingredient in formulated herbicides in units of g/ha.

The control sensitive hybrid and inbred (A and B) were destroyed by all sulfonylurea herbicides tested, except nicosulfuron. Homozygous resistant inbred lines, $BC_3$-$M_4M12$ (I), $BC_3$-$M_4M11$ (J) and $BC_3$-$M_4M7$ (K), were resistant to metsulfuron-methyl, tribenuron-methyl and to a lesser extent triflusulfuron-methyl at 20 g a.i./ha, marginally tolerant to nicosulfuron and less susceptible than the standards to thifensulfuron-methyl and primisulfuron-methyl. All three lines were as susceptible as the standards to rimsulfuron and triasulfuron at the application rates tested. The heterozygous resistant hybrids (C to H) were as tolerant as the three homozygous resistant lines to metsulfuron-methyl and tribenuron-methyl, but the homozygous resistant lines were more tolerant to primisulfuron-methyl, nicosulfuron and thifensulfuron-methyl. These results are indicative of highly heritable (i.e. dominant or semi-dominant type) mutations.

Test B—Evaluation of Resistance to ALS-inhibiting Herbicides

A greenhouse experiment was conducted to evaluate the spectrum of tolerance of three homozygous resistant mutants to various herbicides inhibiting acetolactate synthase (ALS) as their mode of action. The inbred lines tested were the 5th generation self-pollinated maintainers, $M_5M7$, $M_5M11$ and $M_5M12$, as well as the 4th generation male sterile backcrosses $BC_4$-$M_5M7$, $BC_4$-$M_5M11$ and $BC_4$-$M_5M12$. Treatments of formulated herbicides were applied post-emergence at the 4-leaf stage. Application rates of the test herbicides were chosen to coincide with the rates commonly used in the crops for which they are registered. The application rate of imazethapyr was chosen to match the rate recommended to control parasitic weeds in sunflowers by L. Garcia-Torres et al., *Weed Technology* 1995, 9, 819-824. Wild type H89 inbred sunflower was not included in this test, because the many of the tested herbicides are known to be efficacious in controlling volunteer sunflower as a weed. Treatments were replicated twice. The evaluation of the maximum injury to sunflower varieties by sulfonylurea herbicides was measured by visual ratings; mean values are listed in Table 6. A rating of 0% phytotoxicity means no crop injury. A rating of 15 to 20% injury, indicating the plants were not significantly adversely affected and rapidly and completely recovered. A rating of 100% means the complete destruction of all plants.

TABLE 6

Maximum Phytotoxicity Following Herbicide Treatments

| Active Ingredient | Rate (g a.i./ha)* | Sunflower Varieties (described in Table 2) | | | | | |
|---|---|---|---|---|---|---|---|
| | | $M_5M7$ | $M_5M11$ | $M_5M12$ | $BC_4$-$M_5M7$ | $BC_4$-$M_5M11$ | $BC_4$-$M_5M12$ |
| Halosulfuron-methyl | 45 | 50 | 60 | 60 | 60 | 65 | 65 |
| Flupyrsulfuron-methyl-sodium | 10 | 62.5 | 50 | 57.5 | 42.5 | 60 | 50 |
| Amidosulfuron | 30 | 52.5 | 60 | 45 | 47.5 | 57.5 | 55 |
| Tribenuron-methyl | 22.5 | 12.5 | 0 | 7.5 | 10 | 17.5 | 20 |
| Rimsulfuron | 15 | 52.5 | 65 | 55 | 45 | 47.5 | 65 |
| Sulfosulfuron | 22.5 | 50 | 60 | 65 | 47.5 | 57.5 | 50 |
| Ethametsulfuron-methyl | 15 | 10 | 0 | 0 | 5 | 10 | 0 |
| Chlorsulfuron | 20 | 47.5 | 50 | 45 | 45 | 50 | 45 |
| Imazethapyr (ammonium salt) | 25 | 22.5 | 30 | 22.5 | 20 | 25 | 30 |
| Pyrithiobac-sodium | 70 | 37.5 | 50 | 40 | 35 | 42.5 | 40 |

*Application rates in treatments refer to amount of active ingredient in formulated herbicides in units of g/ha.

The results confirmed the good tolerance of the homozygous progeny of the three mutant sources to tribenuron-methyl. All mutants were also found extremely resistant to ethametsulfuron-methyl. A marginal tolerance to a low use rate of imazethapyr was observed. However, as similar marginal tolerance to imazethapyr is also exhibited by non-sulfonylurea-resistant sunflower germplasm, the observed marginal tolerance cannot be considered to be caused by the sulfonylurea-resistance mutations. The mutants were found to be somewhat sensitive to rimsulfuron, halosulfuron-methyl, flupyrsulfuron-methyl (sodium salt), amidosulfuron, sulfosulfuron, chlorsulfuron and pyrithiobac-sodium.

Test C—Evaluation of Sulfonylurea Phytotoxicity to Hybrid Resistant Sunflower

A phytotoxicity test was performed in an outdoors field plot using hybrids $BC_4$-$M_5M7$ (female parent)×PHA155 restorer line (male parent) and $BC_4$-$M_5M12$ (female parent)× PHA155 restorer line (male parent), wherein the tolerance of each hybrid is possibly based on separate mutagenesis events. PHA155 is a restorer line developed by Pioneer Hi-Bred International that can be used as a male parent in crosses with cytoplasmic male sterile (CMS) sunflower lines.

The test herbicides were applied as formulated compositions post-emergence at the sunflower 6-leaf stage in three randomly distributed replications. For the post-emergence applications the test herbicides were applied in an aqueous tank mix solution containing 0.1% v/v Witco Trend 90® ethoxylated fatty alcohol surfactant. Also, two sulfonylurea (tribenuron-methyl and metsulfuron-methyl) seed coating treatments using formulated herbicides were studied in this test, again using three replications. The evaluation of the injury to sunflower varieties by sulfonylurea herbicides was measured by visual ratings; mean values are listed in Table 7. A rating of 0% phytotoxicity means no crop injury. A rating of 15 to 20% injury indicates the plants were not significantly adversely affected and rapidly and completely recovered. A rating of 100% means the complete destruction of all plants.

from the soil. Various herbicide treatments were evaluated using six replications of each treatment. Treatments investigated the following modes of application: seed coating, pre-emergence soil incorporation, bare-ground pre-emergence broadcast application, and post-emergence broadcast application. All herbicide treatments used formulated herbicide compositions.

Seed Coating

For seed coating treatments, 3 mg of *Orobanche cumana* seeds were added to each pot containing a growing mixture of 60% dry loamy soil, 20% sand and 20% of peat, the growing mixture having an organic matter content of 4.2% and a pH of 8.05. The pots were placed in plastic trays and watered to the extent of 25% of soil weight. Pots were kept in a greenhouse for 8 to 10 days at about 24° C. during the day and 20° C. at night. Eight seeds of $BC_4$-$M_5M12$ sunflower resistant mutant

TABLE 7

Phytotoxicity to $BC_4$-$M_5M7$ × PHA155 and $BC_4$-$M_5M12$ × PHA155 Hybrids Following Herbicide Treatments

| | | Rating After Treatment | | | | | |
|---|---|---|---|---|---|---|---|
| | | $BC_4$-$M_5M7$ × PHA155 | | | $BC_4$-$M_5M12$ × PHA155 | | |
| Active Ingredient | Rate* | 7 DAT† | 15 DAT | 30 DAT | 7 DAT | 15 DAT | 30 DAT |
| Postemergence: | | | | | | | |
| Tribenuron-methyl | 11.25 | 25 | 20 | 8 | 17 | 18 | 8 |
| Tribenuron-methyl | 22.5 | 37 | 38 | 22 | 22 | 18 | 13 |
| Metsulfuron-methyl | 3 | 28 | 28 | 15 | 23 | 23 | 22 |
| Metsulfuron-methyl | 6 | 55 | 58 | 43 | 43 | 50 | 33 |
| Triflusulfuron-methyl | 7.5 | 38 | 40 | 28 | 22 | 22 | 25 |
| Triflusulfuron-methyl | 15 | 57 | 53 | 40 | 38 | 45 | 43 |
| Chlorimuron-ethyl | 6.25 | 83 | 73 | 67 | 70 | 80 | 68 |
| Chlorimuron-ethyl | 12.5 | 85 | 83 | 83 | 80 | 90 | 88 |
| Nicosulfuron | 18.75 | 37 | 40 | 18 | 28 | 20 | 18 |
| Nicosulfuron | 37.5 | 57 | 55 | 50 | 42 | 52 | 50 |
| Rimsulfuron | 15 | 87 | 92 | 93 | 87 | 90 | 90 |
| Seed Treatment: | | | | | | | |
| Tribenuron-methyl | 22.5 | 57 | 38 | 32 | 10 | 23 | 11 |
| Metsulfuron-methyl | 6 | 88 | 73 | 57 | 83 | 75 | 57 |

*Application rates in treatments refer to amount of active ingredient in formulated herbicides in units of g a.i./ha.
†Days after treatment.

The hybrids used in this test were heterozygous in the resistance gene. As shown by the results of Test A, varieties homozygous in the resistance gene can be expected to have greater resistance than the $BC_4$-$M_5M7$×PHA155 and $BC_4$-$M_5M12$×PHA155 hybrids to some of the herbicides used in Test C. The data in Table 7 show the phytotoxicity to these two hybrids was greatest soon after herbicide application and then decreased. For tribenuron-methyl at 11.25 g a.i./ha little injury was evident 30 days after treatment. For post-emergent application to these hybrids, tribenuron-methyl was found to be the most selective sulfonylurea, followed by metsulfuron-methyl, nicosulfuron, triflusulfuron-methyl, chlorimuron-ethyl and rimsulfuron. Post-emergent application to these hybrids was less phytotoxic than seed-coating.

Test D—Use of Sulfonylureas to Control *Orobanche cumana* in Resistant Sunflowers Various inbreds or hybrids obtained from the M7 and M12 resistant mutants were used to demonstrate control of the parasitic weed species *Orobanche cumana*. The purpose of this test was to evaluate the efficacy of tribenuron-methyl to control *Orobanche cumana* before and after crop emergence were sown manually in the pots contaminated with *Orobanche*, at the end of the incubation period of the parasitic weed seeds.

Before sowing, the sunflower seeds were coated with a formulated composition containing 25% tribenuron-methyl. Seeds were first coated using a table-top laboratory fluid bed equipped with a coating device ("Strea I Aerocoater" made by Niro Aeromatic, Haupstrasse 145, CH4416 Bubendorf, Switzerland) and a coating solution containing about 23% Sepiret 8330® (coating composition sold by Seppic, 75 quai d'Orsay Paris 75321 cedex 07 France) and 77% water at the rate of 3 L/100 Kg of seeds. After coating, the seeds were dried in a fluid bed drier at 35° C. Then the seeds were sealed in a plastic bag containing an aqueous solution amounting to 5% of the seed weight containing the tribenuron-methyl composition. The quantity of tribenuron-methyl was 0.00001, 0.1 or 10 mg a.i./g of seed. The bag was thoroughly agitated for 3 minutes to uniformly distribute the tribenuron-methyl solution over the seed surfaces. The coated seeds were then dried at ambient temperature and stored until sowing. The maximum concentration was chosen to give a use rate similar to the maximum rate of tribenuron-methyl used in Europe for weed control in cereal crops.

Pre-emergence Soil Incorporation

For treatments using pre-emergence soil incorporation, an aqueous mixture of the tribenuron-methyl composition was sprayed onto soil containing *Orobanche cumana* seeds. The soil was then thoroughly mixed by hand and dispensed into the pots. The quantities of tribenuron-methyl used in these treatments are expressed in g a.i./ha based on the soil volume and pot dimensions. The quantities applied were 11.25 and 22.5 g a.i./ha.

Pre-emergence Broadcast Application

For pre-emergence broadcast applications, two days after sowing of sunflower seeds the pots were sprayed with an aqueous mixture of the tribenuron-methyl composition at application rates of 11.25 and 22.5 g a.i./ha.

Post-emergence Broadcast Application

For post-emergence broadcast applications, at the 6 to 8 leaf sunflower stage the pots were sprayed with an aqueous mixture of the tribenuron-methyl composition at application rates of 2.25 and 11.25 g a.i./ha.

Evaluation

The effect of the various treatments was evaluated 35 days after sowing. The sunflower roots were cleaned by washing in water, and the presence of *Orobanche* nodules was determined visually and by weighing root wet mass in comparison to check plants free of *Orobanche* infestation. Compared to the nodules observed in the check plants, the controlled *Orobanche* nodules displayed no growth and a brownish color, and lacked a white growing stem apex. The nodules caused by *Orobanche* increased root weight, and a correlation (r=0.7) was found between visual scores and weight measurements. Thus the weighing technique could be used to corroborate visual efficacy scorings. *Orobanche* emergence was also scored but found to be less useful to evaluate treatment efficiency at the evaluation timing of this test. The results of these treatments are listed in Table 8.

TABLE 8

Descriptions of *Orobanche* Treatments using Tribenuron-methyl and Results

| Seed coating (mg a.i./g) | | | Pre-emergence soil incorporation (g a.i./ha) | | Pre-emergence broadcast spray (g a.i./ha) | | Post-emergence broadcast spray (g a.i./ha) | | Control (%) |
|---|---|---|---|---|---|---|---|---|---|
| 0.00001 | 0.1 | 10 | 11.25 | 22.5 | 11.25 | 22.5 | 2.25 | 11.25 | |
| | | | | | | | | | 0 |
| X | | | | | | | | | 8 |
| | X | | | | | | | | 37 |
| | | X | | | | | | | 82 |
| X | | | | | | | X | | 63 |
| X | | | | | | | | X | 70 |
| | X | | | | | | | X | 85 |
| | X | | | | | | | X | 80 |
| | | X | | | | | X | | 82 |
| | | X | | | | | | X | 89 |
| | | | X | | | | | | 55 |
| | | | | X | | | | | 72 |
| | | | | | X | | | | 40 |

TABLE 8-continued

Descriptions of *Orobanche* Treatments using Tribenuron-methyl and Results

| Seed coating (mg a.i./g) | | | Pre-emergence soil incorporation (g a.i./ha) | | Pre-emergence broadcast spray (g a.i./ha) | | Post-emergence broadcast spray (g a.i./ha) | | Control (%) |
|---|---|---|---|---|---|---|---|---|---|
| 0.00001 | 0.1 | 10 | 11.25 | 22.5 | 11.25 | 22.5 | 2.25 | 11.25 | |
| | | | | | | X | | X | 78 |
| | | | | | | | X | | 63 |
| | | | | | | | | X | 88 |

As single applications, seed-coatings and post-emergent applications gave the best control of *Orobanche*. Seed coating using 10 mg a.i./g of seed or post-emergence application of 11.25 g a.i./ha each gave over 80% control of *Orobanche* as measured by effect on roots. Combining modes of application allowed lowering rates for each application mode or at the same rates gave greater control. The best overall treatment, giving 89% control, was 10 mg a.i./g seed coating followed by a post-emergence application of 11.25 g a.i./ha Test E—Use of Sulfonylureas to Control *Orobanche cumana* in Resistant Sunflowers Based on the results from Test D, a modified protocol was developed to include three timings of post-emergence treatment. The hybrid $BC_4$-$M_5M12$ (female parent)×PHA155 restorer line (male parent) described in Test C was used in this test. Various herbicide programs were tested using three replications. A tribenuron-methyl herbicide formulated composition was applied at 11.5 and 22.5 g a.i./ha, and a metsulfuron-methyl formulated herbicide composition was applied at 3 and 6 g ai./ha. Seed coatings of these formulated herbicides were applied to 6 kg of seeds in such amount that considering the distribution of the coated seeds in each pot, the herbicide active ingredient (a.i.) application rates per hectare were as indicated.

The treatments were applied similar to the methods described for Test D. Pre-emergence applications were broadcast only, not soil incorporated. For pre-emergence application, the pots were sprayed using the high rates of the herbicides two days after sowing the sunflower seeds. Post-emergence treatments were applied at the 4-6 leaf stage of sunflower (corresponding to early stage of *Orobanche* attachment; identified as "T1"), the 6-8 leaf stage of sunflower (corresponding to the mid stage of *Orobanche* attachment; nodules<5 mm diameter; identified as "T2") and 8-12 leaf stage of sunflower (corresponding to late stage of *Orobanche* attachment; identified as "T3"). The mid-stage applications included the high as well as low application rates of each herbicide.

For comparison were also included in this test other acetolactate synthase-inhibiting herbicides reported in the literature as giving good weed control of *Orobanche* (L. Garcia-Torres et al., *Weed Research* 1994, 34, 395-402; L. Garcia-Torres et al., *Weed Technology* 1995, 9, 819-824; J. Hershenhorn et al., *Weed Technology* 1998, 12, 108-114).

The results were evaluated as described for Test D and are listed in Table 9.

TABLE 9

Orobanche Treatments and Results

| Herbicide | Seed coating (g a.i./ha) | Pre-emergence (g a.i./ha) | Post-emergence (g a.i./ha) | Timing | Control (%) | Injury (%) |
|---|---|---|---|---|---|---|
| Tribenuron-methyl | | 22.5 | | | 70 | 70 |
| Metsulfuron-methyl | | 6 | | | — | 100 |
| Tribenuron-methyl | 11.25 | | 11.25 | T2 | 88 | 50 |
| Metsulfuron-methyl | 3 | | 3 | T2 | — | 100 |
| Tribenuron-methyl | | | 22.5 | T2 | 75 | 0 |
| Metsulfuron-methyl | | | 6 | T2 | 97 | 25 |
| Tribenuron-methyl | | | 11.25 + 11.25 | T1 + T3 | 90 | 0 |
| Metsulfuron-methyl | | | 3 + 3 | T1 + T3 | 96 | 0 |
| Tribenuron-methyl | | 11.25 | 11.25 | T2 | 78 | 0 |
| Metsulfuron-methyl | | 3 | 3 | T2 | 87 | 0 |
| Tribenuron-methyl | | 22.5 | | | 0 | 0 |
| Metsulfuron-methyl | | 6 | | | 30 | 0 |
| Chlorsulfuron | | 2 | | | 13 | 0 |
| Chlorsulfuron | | 10 | | | 58 | 0 |
| Imazethapyr, ammonium salt | | 40 | | | 60 | 0 |
| Imazapyr, isopropylamine salt | | | 15 | T3 | 72 | 0 |
| Triflusulfuron-methyl | | | 18.75 | T2 | 75 | 0 |

The treatments involving pre-emergence application only had little effect on *Orobanche* at the rates tested, possibly because limited watering of the soil did not cause the herbicides to reach the sunflower roots. The treatments involving seed coating had substantial effect on *Orobanche*, but were considerably phytotoxic at these application rates to the sunflower varieties in this test.

The treatments involving post-emergence application gave the best results in this test. Metsulfuron-methyl was found to be both more efficacious in controlling *Orobanche* and more likely to cause sunflower phytotoxicity even at lower application rates than tribenuron-methyl. A split application of metsulfuron-methyl of 3 g a.i./ha each at T1 and T3 provided the same excellent level of *Orobanche* control as 6 g a.i./ha at T2 while eliminating sunflower phytotoxicity.

Chlorsulfuron, imazethapyr, imazapyr and triflusulfuron-methyl were less efficacious in controlling *Orobanche*. Imazapyr and triflusulfuron-methyl caused transitory phytotoxicity symptoms, but the sunflowers recovered completely.

Test F—Sequential Application of Sulfonylureas to Control *Orobanche cumana*

A greenhouse experiment was performed to identify the best sequential program compared to straight application of tribenuron-methyl or metsulfuron-methyl for control of *Orobanche cumana* (Race F). The dose range for optimum efficacy was also studied. Both herbicides were used as formulated compositions. The two hybrids $BC_4$-$M_5M7$ (female parent)×PHA155 restorer line (male parent) and $BC_4$-$M_5M12$ (female parent)×PHA155 restorer line (male parent) described in Test C were used in this test. $BC_4$-$M_5M7$×PHA155 is referred to below as "Hybrid 7", and $BC_4$-$M_5M12$×PHA155 is referred to below as "Hybrid 12".

Seed coating treatment was performed as described for Test D. Post-emergence treatments were applied at the 2-4 leaf stage of sunflower (corresponding to early stage of *Orobanche* attachment; identified as "T1"), the 6 leaf stage of sunflower (corresponding to the mid stage of *Orobanche* attachment; nodules<5 mm diameter; identified as "T2") and 8 leaf stage of sunflower (corresponding to late stage of *Orobanche* attachment; identified as "T3").

Imazapyr, which is an imidazolinone instead of a sulfonylurea but also inhibits acetolactate synthase, was included for reference as it has been reported to control *Orobanche* in sunflower (L. Garcia-Torres et al., *Weed Technology* 1995, 9, 819-824).

The efficacy was evaluated visually as described for Test D except that the efficacy was assessed ten days later than for Tests D and E. The later evaluation allowed observing any reduction of efficacy due to late *Orobanche* emergence or re-growth of treated nodules. Efficacy in controlling *Orobanche* attached to roots was evidenced by nodules comprising black necrotic tissues with no apparent active meristematic area. These nodules could be easily crushed between fingers.

The treatments and results are summarized in Table 10.

TABLE 10

Sequential *Orobanche* Treatments and Results in Hybrid 7 and Hybrid 12

| Herbicide | Seed coating (g a.i./ha) | Post-emergence (g a.i./ha) | | | % Control in Hybrid 7 | % Control in Hybrid 12 |
|---|---|---|---|---|---|---|
| | | T1 | T2 | T3 | | |
| Tribenuron-methyl | 11.25 | | 11.25 | | 77 | 78 |
| | 11.25 | | | 11.25 | 82 | 83 |
| | | | 11.25 | | 77 | 73 |
| | | | | 11.25 | 78 | 80 |
| | | 22.5 | | | 72 | 73 |
| | | | 22.5 | | 82 | 83 |
| | | | | 22.5 | 87 | 87 |
| | | 11.25 | 11.25 | | 85 | 85 |
| Metsulfuron-methyl | 3 | | 3 | | 92 | 90 |
| | 3 | | | | 65 | 63 |
| | | | | 3 | 93 | 95 |
| Imazapyr, isopropylamine salt | | | 15 | | 97 | 97 |

The test showed no benefit to seed coating followed by post-emergence treatment, compared to a single post-emergence treatment. Late post-emergence treatments gave better control than earlier post-emergence treatments, probably because it better matches the elongation phase of *Orobanche* nodule meristem activity. In this greenhouse test, a single late post-emergence treatment with 3 g a.i./ha of metsulfuron-methyl gave excellent control comparable to 15 g a.i./ha of imazapyr. 22.5 g a.i./ha of tribenuron-methyl was needed for good control of *Orobanche*.

Test G—Control of Sulfonylurea-Resistant Sunflowers as Volunteer Weeds

Sunflower crops are often rotated with cereals, such as wheat, or occasionally other crops like sugar beet. As part of their weed control spectrum, sulfonylurea herbicides are often used to remove volunteer sunflower plants appearing in rotational crops. The purpose of this test was to evaluate herbicides that can be used to control sulfonylurea-resistant sunflower plants appearing as volunteer weeds.

This test involved sulfonylurea-resistant sunflower progeny $BC_2$-$M_3M11$ and $BC_2$-$M_3M12$, derived from M11 and M12, respectively. Also, a sulfonylurea-susceptible hybrid, H89A×RHA274, was included for comparison. Plants were sprayed with formulated herbicides at the 4-leaf stage. The efficacy of the treatments on the sunflowers was visually rated 4 weeks after application, using a scale where 0 means no control of the sunflowers, 85 means sufficient efficacy level to stop plants from flowering and propagating, and 100 means a complete destruction of the mutants. The responses are listed in Table 11.

TABLE 11

Effect of Various Herbicides on Ordinary and Sulfonylurea-Resistant Sunflower

| Treatment | Rate (g a.i./ha) | Efficacy on H89A × RHA274 | Efficacy on $BC_2$-$M_3M11$ | Efficacy on $BC_2$-$M_3M12$ |
|---|---|---|---|---|
| Thifensulfuron-methyl | 10 | 100 | 2 | 10 |
| | 20 | 100 | 17 | 16 |
| | 40 | 100 | 50 | 32 |
| | 60 | 100 | 74 | 58 |
| Tribenuron-methyl | 10 | 100 | 0 | 0 |
| | 20 | 100 | 0 | 0 |
| | 40 | 100 | 3 | 0 |
| | 60 | 100 | 10 | 14 |
| Metsulfuron-methyl | 4 | 100 | 8 | 18 |
| Triflusulfuron-methyl | 15 | 82 | 13 | 8 |
| Phenmedipham | 240 | 0 | 0 | 7 |
| 2,4-D | 530 | 100 | 100 | 100 |
| Thifensulfuron-methyl + Metsulfuron-methyl | 40 + 4 | 100 | 83 | 100 |
| Thifensulfuron-methyl + Tribenuron-methyl | 20 + 10 | 100 | 26 | 26 |
| | 40 + 20 | 100 | 76 | 60 |
| Metsulfuron-methyl + 2,4-D | 4 + 530 | 100 | 100 | 100 |
| Triflusulfuron-methyl + Phenmedipham | 15 + 240 | 100 | 40 | 63 |

The results confirm the excellent to very good level of resistance of the mutants originating from M11 and M12 to tribenuron-methyl up to 60 g a.i./ha. The data also confirm the tolerance of the mutants to metsulfuron-methyl, triflusulfuron-methyl and thifensulfuron-methyl (which was used in the original artificial selection), but to a lesser extent than with tribenuron-methyl.

The combination of thifensulfuron-methyl with metsulfuron-methyl showed good efficacy against the mutants, whereas the combination of thifensulfuron-methyl with tribenuron-methyl was insufficiently active at either application rate to be useful for control of sulfonylurea-resistant sunflower in rotational cereal crops, in which herbicides are typically applied only once during the growing season. The responses of both mutants to 2,4-D, frequently used for weed control in cereals, were exactly the same as with sulfonylurea-susceptible sunflower; the mutants were completely destroyed by 2,4-D alone or in combination with metsulfuron-methyl.

Phenmedipham, used for weed control in sugar beet, was ineffective alone for controlling either sulfonylurea-susceptible or sulfonylurea-resistant volunteer sunflowers. However, when combined with triflusulfuron-methyl, efficacy was synergistically improved, as compared to straight triflusulfuron-methyl. Weed control in sugar beet requires 2-3 herbicide applications per season to efficiently control weeds in this slow growing crop. Following this agronomic practice, 2-3 applications of mixtures of triflusulfuron-methyl and phenmedipham on volunteer sunflower mutants will likely sufficiently retard their growth to prevent flowering and propagation.

Test H—Control of Sunflower Weeds

This test measured the effect of three sulfonylurea herbicides (tribenuron-methyl, metsulfuron-methyl and ethametsulfuron-methyl) as well as two comparison herbicides (imazapyr, isopropylamine salt and aclonifen) for controlling weeds agronomically important in sunflower crops at application rates typical of use of these herbicides in other crops.

Field plots (2 m×5 m) were tilled to remove weed cover and then seeded in rows with the following weeds: *Capsella bursa pastoris, Atriplex patula, Chenopodium album, Stellaria media, Mecurialis annua, Polygonum persicaria, Amaranthus retroflexus, Polygonum convolvulus, Polygonum aviculare, Viola arvensis, Matricaria inodora, Anagallis arvensis, Sinapis arvensis, Setaria viridis, Solanum nigrum* and *Echinochloa crusgalli*. After 21 days from sowing, at which time the weeds had reached the 2- to 6-leaf stage, herbicide treatments were applied to the plots according to a complete randomized block design, with each herbicide treatment triply replicated. The herbicides were sprayed using standard flat fan nozzles moved perpendicular to the sown lines using water spray volumes of about 296 L/ha. For the tribenuron-methyl, metsulfuron-methyl, ethametsulfuron-methyl and imazapyr, isopropylamine salt treatments, 0.1% by volume of Witco Trend® 90 ethoxylated fatty alcohol surfactant adjuvant was added to the spray mixtures to accelerate the herbicidal effect. Tribenuron-methyl was applied at 22.5 g a.i./ha, metsulfuron-methyl was applied at 6 g ai./ha, ethametsulfuron-methyl was applied at 16 g a.i./ha, imazapyr, isopropylamine salt was applied at 15 g a.i./ha, and aclonifen was applied at 1200 g a.i./ha.

Assessments of weed control were made by visual inspection 36 days after herbicide treatment. A visual rating system was used based on a percentage scale from 0 to 100% compared to an adjacent untreated control plot. On this scale 0 represents no visual differences relative to an untreated control and 100 represents complete control of the given weed species. Results are listed in Table 12.

TABLE 12

Effect of Herbicides on Weeds Agronomically Important in Sunflower Crops

| Weed species | Tribenuron-methyl | Metsulfuron-methyl | Ethametsulfuron-methyl | Imazapyr, isopropyl-amine salt | Aclonifen |
|---|---|---|---|---|---|
| *Capsella bursa pastoris* | 100 | 100 | 100 | 100 | 100 |
| *Atriplex patula* | 100 | 100 | 0 | 85 | 0 |

TABLE 12-continued

Effect of Herbicides on Weeds Agronomically Important in Sunflower Crops

| Weed species | Tribenuron-methyl | Metsulfuron-methyl | Ethametsulfuron-methyl | Imazapyr, isopropyl-amine salt | Aclonifen |
|---|---|---|---|---|---|
| *Chenopodium album* | 100 | 100 | 0 | 87 | 100 |
| *Stellaria media* | 100 | 100 | 79 | 100 | 100 |
| *Mercurialis annua* | 100 | 100 | 0 | 47 | 50 |
| *Polygonum persicaria* | 100 | 100 | 0 | 100 | 70 |
| *Amaranthus retroflexus* | 93 | 99 | 82 | 84 | 40 |
| *Polygonum convolvulus* | 93 | 92 | 0 | 94 | 23 |
| *Polygonum aviculare* | 90 | 100 | 0 | 0 | 30 |
| *Viola arvensis* | 100 | 100 | 0 | 0 | 57 |
| *Matricaria inodora* | 100 | 100 | 67 | 43 | 0 |
| *Anagallis arvensis* | 100 | 100 | 100 | 100 | 100 |
| *Sinapis arvensis* | 100 | 100 | 97 | 100 | 100 |
| *Setaria viridis* | 65 | 47 | 0 | 93 | 40 |
| *Solanum nigrum* | 100 | 97 | 70 | 100 | 20 |
| *Echinochloa crus-galli* | 65 | 47 | 33 | 27 | 0 |

The results listed in Table 12 show both tribenuron-methyl and metsulfuron-methyl provide excellent broad-spectrum weed control at application rates to which other tests show the sunflower lines of the invention are tolerant.

DEPOSITS

Deposits of sunflower lines M7, M11, M12 and PHA155 have been maintained by Pioneer Hi-Bred International, Inc., 800 Capital Square, 400 Locust Street, Des Moines, Iowa 50309-2340 U.S.A. since prior to the filing date of this application. On Aug. 2, 2000, Applicants made deposits of sunflower line M7 with American Type Culture Collection (ATCC), Manassas, Va. 20110 U.S.A. consisting of at least 2500 seeds each of cytoplasmic male sterile form SU7F (ATCC Deposit No. PTA-2296) and the complementary line maintainer form SU7G (ATCC Deposit No. PTA-2295). Applicants also deposited with ATCC on Aug. 2, 2000 at least 2500 seeds of restorer sunflower line PHA155 (ATCC Deposit No. PTA-2294). On Dec. 8, 2000, Applicants made deposits with the ATCC depository of sunflower line M11 consisting of at least 250 seeds each of cytoplasmic male sterile form SU11F (ATCC Deposit No. PTA-2767) and the complementary line maintainer form SU11G (ATCC Deposit No. PTA-2768), and sunflower line M12 consisting of at least 250 seeds each of SU12F (ATCC Deposit No. PTA-2769) and SU12G (ATCC Deposit No. PTA-2770), each believed to comprise primarily the restorer form of line M12. These deposits of sunflower lines SU7F & SU7G (M7), SU11F & SU11G (M11), SU12F & SU12G (M12) and PHA155 will be maintained in the ATCC depository, which is a public depository, for a period of 30 years, or for 5 years after the most recent request, whichever is longer, and will be replaced if it becomes nonviable during that period. Additionally, Applicants have satisfied all the requirements of 37 C.F.R. §§ 1.801-1.809, including providing an indication of the viability of the samples. Applicants impose no restrictions on the availability of the deposited material from the ATCC after the issuance of a patent from this application. However, Applicant has no authority to wave any restrictions imposed by law on the transfer of biological material or its transportation in commerce. Applicant does not waive any infringement of Applicant's rights granted under this patent or under the Plant Variety Protection Act (7 USC. 2321 et seq.). Additional deposits of sunflower lines M11 and M12 will be made at the ATCC as needed to ensure availability subject to the conditions herein described above for the SU7F, SU7G and PHA155 deposits.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A sunflower seed, produced from sunflower line M7 comprising a M7 ALS gene, its progeny or the progeny of succeeding generations, bred by either self or cross pollination, which comprises the M7 ALS gene encoding SEQ ID NO: 1 conferring tolerance to sulfonylurea herbicides contained within sunflower line M7, representative seed of said line M7 having been deposited under ATCC Deposit Nos. PTA-2295 and PTA-2296.

2. A sunflower plant, or a part thereof, containing the M7 ALS gene encoding SEQ ID NO: 1 conferring tolerance to sulfonylurea herbicides, grown from the seed of claim 1.

3. The seed of claim 1, further containing a trait conferring resistance to *Orobanche* parasitism.

4. Pollen of the plant of claim 2, wherein the pollen contains the M7 ALS gene encoding SEQ ID NO: 1 conferring tolerance to sulfonylurea herbicides.

5. An ovule of the plant of claim 2, wherein the ovule contains the M7 ALS gene encoding SEQ ID NO: 1 conferring tolerance to sulfonylurea herbicides.

6. A tissue culture of regenerable cells from the plant of claim 2, wherein the cells contain the M7 ALS gene encoding SEQ ID NO: 1 conferring tolerance to sulfonylurea herbicides.

7. A method for producing inbred sunflower seed having tolerance to sulfonylurea herbicides comprising crossing a first parent sunflower plant with a second parent sunflower plant and harvesting the resultant inbred sunflower seed, wherein the first and second parent sunflower plants is the sunflower plant of claim 2.

8. An inbred sunflower seed produced by the method of claim 7.

9. An inbred sunflower plant, or a part thereof, produced by growing the inbred seed of claim 8.

10. A seed produced from the inbred plant of claim 9.

11. A method for producing hybrid sunflower seed containing the M7 ALS gene encoding SEQ ID NO: 1 conferring tolerance to sulfonylurea herbicides comprising crossing a first parent sunflower plant with a second parent sunflower plant and harvesting the resultant hybrid sunflower seed, wherein the first or second parent sunflower plant is the sunflower plant of claim 2.

12. A hybrid sunflower seed produced by the method of claim 11.

13. A hybrid sunflower plant, or a part thereof produced by growing the hybrid seed of claim 12.

14. A seed produced from the hybrid plant of claim 13.

15. A method for controlling undesired vegetation in a crop of sunflower plants of any one of claim 2, 9 or 13 comprising applying to the locus of the vegetation an effective amount of a sulfonylurea herbicide.

16. The method of claim 15, wherein the undesired vegetation comprises a parasitic weed.

17. The method of claim 16, wherein the parasitic weed is an *Orobanche* species.

18. The method of claim 15, wherein the sulfonylurea herbicide is tribenuron-methyl.

19. The method of claim 15, wherein the sulfonylurea herbicide is metsulfuron-methyl.

20. The method of claim 15, wherein the sulfonylurea herbicide is ethametsulfuron-methyl.

21. The method of claim 15, wherein the sulfonylurea herbicide is applied post-emergence to the crop of sunflower plants.

22. A method for controlling volunteer sunflower plants of any one of claim 2, 9 or 13 in a cereal crop comprising applying to the locus of the volunteer sunflower plants an effective amount of 2,4-D.

23. A method of controlling volunteer sunflower plants of any one of claim 2, 9 or 13 in a sugar beet crop comprising applying to the locus of the volunteer sunflower plants an effective amount of a mixture of triflusulfuron-methyl and phenmedipham.

\* \* \* \* \*